(12) United States Patent
Mitamura

(10) Patent No.: US 10,105,037 B2
(45) Date of Patent: Oct. 23, 2018

(54) INSERTION DEVICE

(71) Applicant: OLYMPUS CORPORATION, Tokyo (JP)

(72) Inventor: Yuki Mitamura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/478,743

(22) Filed: Apr. 4, 2017

(65) Prior Publication Data

US 2017/0202434 A1 Jul. 20, 2017

Related U.S. Application Data

(63) Continuation of application No. PCT/JP2016/060220, filed on Mar. 29, 2016, now abandoned.

(30) Foreign Application Priority Data

Jul. 9, 2015 (JP) .................................. 2015-137765

(51) Int. Cl.
*A61B 1/00* (2006.01)
*G02B 23/24* (2006.01)

(52) U.S. Cl.
CPC ........ *A61B 1/0016* (2013.01); *A61B 1/00135* (2013.01); *A61B 1/00154* (2013.01); *A61B 1/00156* (2013.01); *G02B 23/2476* (2013.01)

(58) Field of Classification Search
CPC .............. A61B 1/0016; A61B 1/00154; A61B 1/00071; A61B 1/00133; A61B 1/00087;

(Continued)

(56) References Cited

U.S. PATENT DOCUMENTS

2005/0272976 A1 12/2005 Tanaka et al.
2012/0029281 A1* 2/2012 Frassica ............ A61B 1/00082
600/114
2014/0330079 A1 11/2014 Ishizaki et al.

FOREIGN PATENT DOCUMENTS

CN 103889303 A 6/2014
JP 2005-253892 A 9/2005
(Continued)

OTHER PUBLICATIONS

English translation of International Preliminary Report on Patentability dated Jan. 18, 2018 together with the Written Opinion received in related International Application No. PCT/JP2016/060220.

(Continued)

*Primary Examiner* — Timothy J Neal
(74) *Attorney, Agent, or Firm* — Scully, Scott, Murphy & Presser, P.C.

(57) ABSTRACT

On an inner peripheral surface of an assistance tool of an insertion device, a sliding surface extends from an assistance tool proximal surface toward a distal side, and when the assistance tool attached to an insertion section rotates, the sliding surface slides on a supporting surface around a longitudinal axis. A flange portion of the insertion section includes an opposed surface opposed to the assistance tool proximal surface with a gap when the assistance tool is attached to the insertion section. In a part where the assistance tool proximal surface is opposed to the opposed surface, a proximal end of an outer peripheral surface of the assistance tool does not form a step relative to the flange portion.

5 Claims, 4 Drawing Sheets

(58) Field of Classification Search
CPC ............ A61B 1/00128; A61B 1/00135; A61B 1/00073; A61B 1/00075; A61B 1/00082; A61B 1/0014; A61B 1/00158; A61B 1/0055; A61B 1/31; A61B 1/018; G02B 23/2476

See application file for complete search history.

(56) References Cited

FOREIGN PATENT DOCUMENTS

| | | |
|---|---|---|
| WO | WO 2012/137364 A1 | 10/2012 |
| WO | WO 2014/208333 A1 | 12/2014 |
| WO | WO 2014/208334 A1 | 12/2014 |

OTHER PUBLICATIONS

International Search Report dated Jun. 28, 2016 issued in PCT/JP2016/060220.

Japanese Office Action dated Nov. 22, 2016 issued in JP 2016-560945.

Chinese Office Action dated Feb. 1, 2018 in Chinese Patent Application No. 201680003610.4.

\* cited by examiner

INSERTION DEVICE

CROSS-REFERENCE TO RELATED APPLICATIONS

This is a Continuation Application of PCT Application No. PCT/JP2016/060220, filed Mar. 29, 2016 and based upon and claiming the benefit of priority from prior Japanese Patent Application No. 2015-137765, filed Jul. 9, 2015, the entire contents of which are incorporated herein by reference.

BACKGROUND OF THE INVENTION

1. Field of the Invention

The present invention relates to an insertion instrument which is provided with an insertion section extending along the longitudinal axis, and to an assistance tool which is attached to the insertion section of the insertion instrument and which rotates around the longitudinal axis when a driving force is transmitted.

2. Description of the Related Art

U.S. Patent Application Publication No. 2014/0330079 discloses a spiral unit (assistance tool) attached to the insertion section of an endoscope (insertion device). The spiral unit (a spiral tube and an outer rotatable cylinder) is detachably attached to the insertion section to cover the outer peripheral of the insertion section, and is provided with a spiral fin spirally extending, with the longitudinal axis of the insertion section as a center. In the insertion section, a rotatable cylinder (an inner rotatable cylinder) is attached to a base portion to be rotatable around the longitudinal axis. A plurality of rollers are attached to the rotatable cylinder, and the insertion section is provided with a projection projected by the rollers toward the outer peripheral side of the insertion section. In the state where the spiral unit is attached to the insertion section, a driving force is transmitted, and the rotatable cylinder and the rollers integrally rotate around the longitudinal axis. As a result, a pushing force acting around the longitudinal axis is applied from the projection of the insertion section to the proximal portion of the spiral unit. Accordingly, a driving force is transmitted to the spiral unit, and the spiral unit rotates around the longitudinal axis relative to the base portion. When the spiral unit rotates, with the spiral fin being pushed by the wall of a lumen or the like toward the inner peripheral side, a propulsion force acting toward the distal side or the proximal side is exerted on the spiral unit and the insertion section. According to U.S. Patent Application Publication No. 2014/0330079, a supporting surface which supports the spiral unit attached to the insertion section is provided on the outer peripheral surface of the insertion section (base portion) in a part on the proximal side with respect to the rotatable cylinder (projection). The inner peripheral surface of the spiral unit is provided with a sliding surface. In the state where the spiral unit attached to the insertion section rotates, the sliding surface slides on the supporting surface of the insertion section around the longitudinal axis.

BRIEF SUMMARY OF THE INVENTION

According to one aspect of the invention, an insertion device including: an insertion section extending along a longitudinal axis; an assistance tool which is attached to the insertion section to cover the insertion section from an outer peripheral side, and which is rotated around the longitudinal axis when a driving force is transmitted thereto; an assistance tool proximal surface forming a proximal end of the assistance tool; a supporting surface which is provided on an outer peripheral surface of the insertion section, and which is configured to support the assistance tool; a sliding surface which is provided on an inner peripheral surface of the assistance tool, and which extends from the assistance tool proximal surface toward a distal side, the sliding surface being configured to slide on the supporting surface, with the longitudinal axis as a center, when the assistance tool attached to the insertion section rotates around the longitudinal axis; a flange portion which is provided on a proximal side with respect to the supporting surface in the insertion section, and which is projected from the supporting surface toward the outer peripheral side, the flange portion including an opposed surface which is opposed to the assistance tool proximal surface with a gap in a direction along the longitudinal axis in a state where the assistance tool is attached to the insertion section; and an assistance tool taper surface which is provided on an outer peripheral surface of the assistance tool, and which extends from the assistance tool proximal surface toward the distal side, the assistance tool taper surface permitting an outer diameter of the assistance tool to increase from the proximal side toward the distal side, and in a state where the assistance tool is attached to the insertion section, the assistance tool taper surface extending from the assistance tool proximal surface while no step being formed relative to the flange portion in a part where the assistance tool proximal surface is opposed to the opposed surface.

According to one another aspect of the invention, an insertion device including: an insertion section extending along a longitudinal axis; an assistance tool which is attached to the insertion section to cover the insertion section from an outer peripheral side, and which is rotated around the longitudinal axis when a driving force is transmitted thereto; an assistance tool proximal surface forming a proximal end of the assistance tool; a supporting surface which is provided on an outer peripheral surface of the insertion section, and which is configured to support the assistance tool; a sliding surface which is provided on an inner peripheral surface of the assistance tool, and which extends from the assistance tool proximal surface toward a distal side, the sliding surface being configured to slid3 on the supporting surface, with the longitudinal axis as a center, when the assistance tool attached to the insertion section rotates around the longitudinal axis; a flange portion which is provided on a proximal side with respect to the supporting surface in the insertion section, and which is projected from the supporting surface toward the outer peripheral side, the flange portion including an opposed surface which is opposed to the assistance tool proximal surface with a gap in a direction along the longitudinal axis in a state where the assistance tool is attached to the insertion section; and an assistance tool diameter-uniform surface which is provided on an outer peripheral surface of the assistance tool, and which extends from the assistance tool proximal surface toward the distal side, the assistance tool diameter-uniform surface permitting an outer diameter of the assistance tool to be uniform in the direction along the longitudinal axis, and in a state where the assistance tool is attached to the insertion section, the assistance tool diameter-uniform surface extending from the assistance tool proximal surface while no step being formed relative to the flange portion in a part where the assistance tool proximal surface is opposed to the opposed surface.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

Figure 1:
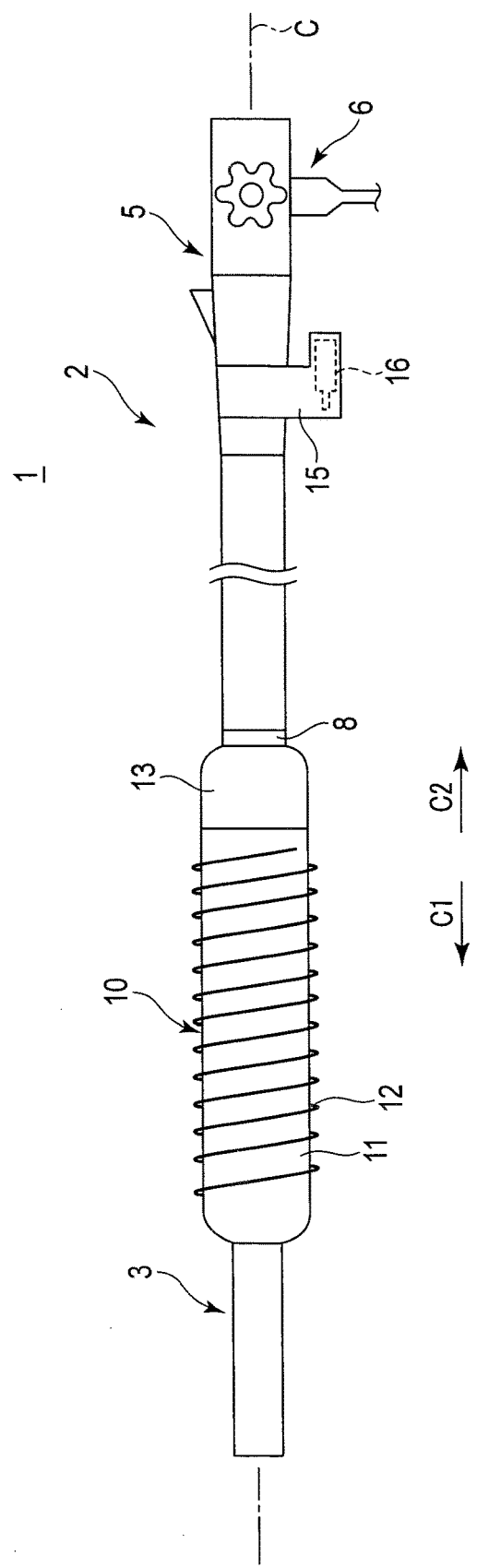
FIG. 1 is a schematic view illustrating an endoscope device according to the first embodiment.

The first embodiment of the present invention will be described with reference to FIGS. 1 to 3. FIG. 1 is a diagram illustrating an endoscope device 1, which is an insertion device according to the present embodiment.

As shown in FIG. 1, the endoscope device 1 includes an endoscope 2 which is an insertion instrument, and a spiral unit 10 which is an assistance tool. The endoscope 2 includes an insertion section 3, and the insertion section 3 has a longitudinal axis C. One side of a direction along the longitudinal axis C is a distal side (side indicated by arrow C1 in FIG. 1), while the side opposite to the distal side is a proximal side (side indicated by arrow C2 in FIG. 1). The insertion section 3 extends along the longitudinal axis C from the proximal side to the distal side. The endoscope 2 is provided with an operation section 5 located on the proximal side of the insertion section 3. The endoscope 2 includes a universal cord 6 connected at one end to the operation section 5. Via the universal cord 6, the endoscope 2 is connected to peripheral devices unit, including an image processing device (not shown), a light source device (not shown), a drive control device (not shown), an operation input device (not show) such as a foot switch, and a display device (not shown) such as a monitor.

An imaging element (not shown) such as a CCD is provided inside the distal portion of the insertion section 3. The imaging element images a subject through an observation window (not shown) formed on the outer surface of the distal portion of the insertion section 3. An image signal is transmitted to the image processing device through an image cable (not shown), which extends through the interior of the insertion section 3, the interior of the operation section 5 and the interior of the universal code 6, and the image processing device performs image processing. As a result, the image processing device generates an image of the subject, and the generated image of the subject is displayed on the display. Light emitted from the light source device is guided by a light guide (not show), which extends through the interior of the insertion section 3, the interior of the operation section 5 and the interior of the universal code 6. The guided light is output from an illumination window (not shown) formed on the outer surface of the distal portion of the insertion section 3, and the subject is irradiated with the light.

The spiral unit 10 includes an extending tube 11 extending along the longitudinal axis C, and a spiral fin 12 provided on the outer peripheral surface of the extending tube 11 and projected outer peripheral side. The spiral fin 12 extends spirally, with the longitudinal axis C as a center. In the spiral unit 10, a cylindrical assistance tool side connecting portion (connector) 13 is coupled to the proximal side of the extending tube 11. The insertion section 3 is provided with a scope side connecting portion 8 to which the assistance tool side connecting portion 13 of the spiral unit 10 is connectable. The spiral unit (assistance tool) 10 is attached to the insertion section 3 by connecting the assistance tool side connecting portion 13 to the scope side connecting portion 8.

A motor casing 15 is attached to the operation section 5, and an electric motor 16, serving as a driving source, is provided inside the motor casing 15. When operation input is performed by an operation input device (not shown), electric power is supplied from the drive control device to the electric motor by way of an electric line (not shown), which extends through the interior of the operation section 5 and the interior of the universal cord 6. As a result, the electric motor 16 is driven. When the electric motor 16 is driven, a driving force, which rotates the spiral unit 10 around the longitudinal axis C, is generated.

Figure 2:
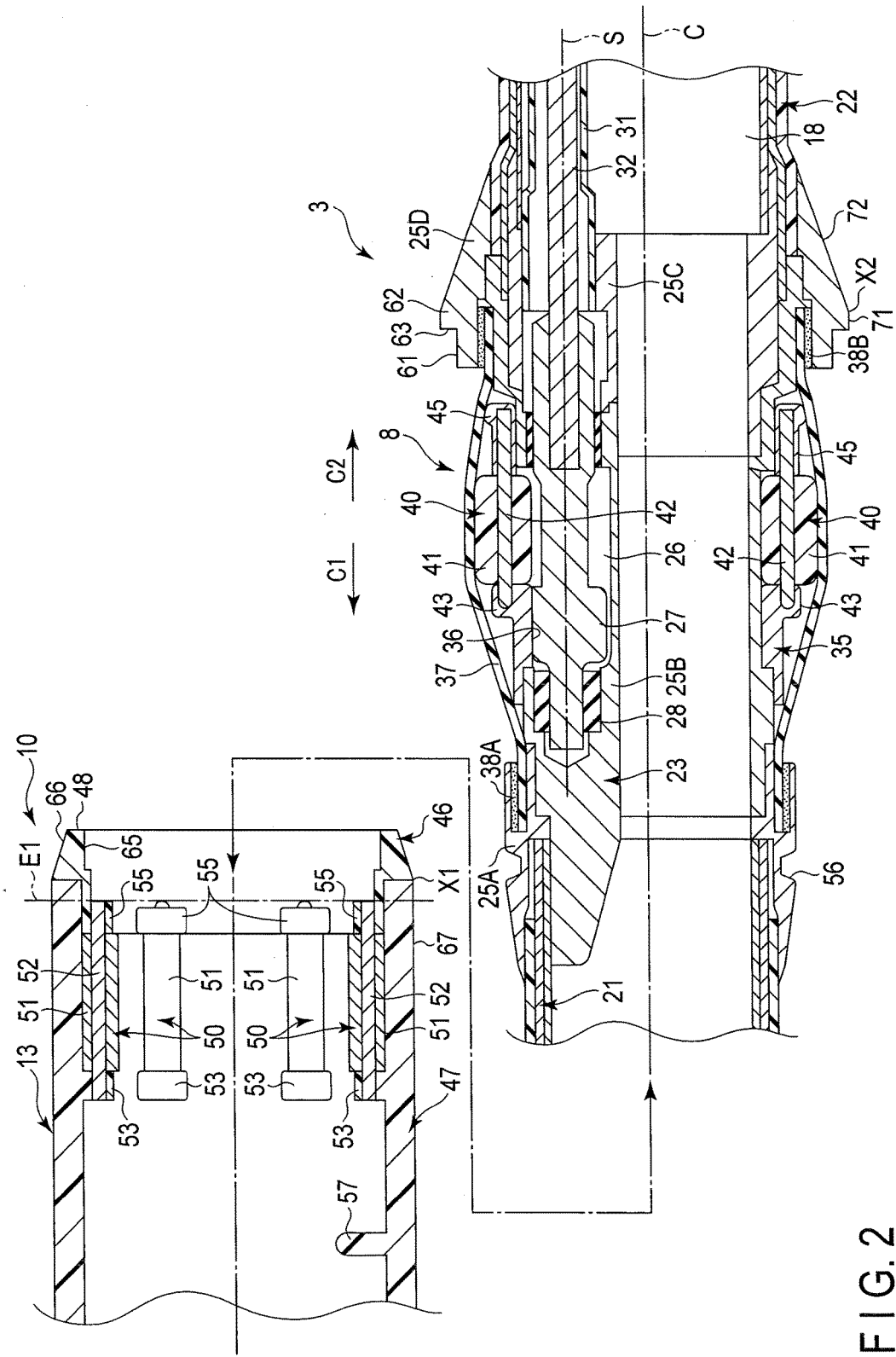
FIG. 2 is a sectional view schematically illustrating configurations of a scope side connecting portion of an insertion section and an assistance tool side connecting portion of a spiral unit in the first embodiment in a section parallel to the longitudinal axis.

FIG. 2 shows a section parallel to the longitudinal axis and illustrates configurations of the scope side connecting portion 8 of the insertion section 3 and the assistance tool side connecting portion 13 of the spiral unit 10. In FIG. 2, illustration of the image cable and the light guide is omitted. As shown in FIG. 2, the insertion section 3 includes a distal side flexible tube section 21, and a proximal side flexible tube section 22 located on the proximal side with respect to the distal side flexible tube section 21. The proximal end of the proximal side flexible tube section 22 is connected to the operation section 5. The distal side flexible tube section 21 and the proximal side flexible tube section 22 are coupled to each other with the scope side connecting portion 8 interposed. The scope side connecting portion 8 includes a base portion 23 formed of a hard material. In the state where the spiral unit 10 is attached to the insertion section 3, the outer peripheral side of the base portion 23 is covered with the assistance tool side connecting portion 13 (the proximal portion of the spiral unit 10). The spiral unit 10 extends toward the distal side from a region located on the outer peripheral side of the base portion 23. In the present embodiment, the base portion 23 is formed by coupling four coupling members 25A to 25C together, but the number of members constituting the base portion 23 is not limited to this. For example, the base portion 23 may be made of a single integral member.

In the insertion section 3, the base portion 23 defines a hollow section 26. The hollow section 26 is opened toward the outer peripheral side, and is opened toward an internal space 18 of the insertion section 3 in which the image cable and the light guide (neither is shown) extend. In the hollow section 26, a driving gear 27 is attached to the base portion 23 (to the coupling member 25B) by means of a support member 28. In the inside (internal space 18) of the proximal side flexible tube section 22, a channel tube 31 extends from the proximal side to the distal side. The distal end of the channel tube 31 is connected to the base portion 23 (to the coupling member 25C). Inside the channel tube 31, a driving shaft 32 extends along a shaft axis S, which is substantially parallel to the longitudinal axis C. The distal end of the driving shaft 32 is inserted into the hollow section 26 and is connected to the driving gear 27. The proximal end of the driving shaft 32 is coupled to the electric motor 16 by means of a gear (not shown) or the like. When the electric motor 16 is driven, a driving force is transmitted to the driving shaft 32, and the driving shaft 32 rotates, with the shaft axis S as a center. As a result, the driving force is transmitted to the driving gear 27, and the driving gear 27 is rotated.

The scope side connecting portion 8 of the insertion section 3 includes a rotatable cylinder 35 which is attached to the base portion 23 in such a manner as to cover the base portion 23 (coupling member 25B) from the outer peripheral side. The rotatable cylinder 35 is rotatable around the longitudinal axis C relative to the base portion 23. The rotatable cylinder 35 is provided with an inner peripheral gear portion 36 on the inner peripheral surface thereof. The inner peripheral gear portion 36 is formed over the whole circumference around the longitudinal axis C. The driving gear 27 is in mesh with the inner peripheral gear portion 36 in the hollow section 26. With this structure, when the driving gear 27 rotates, a driving force is transmitted to the rotatable cylinder 35, and the rotatable cylinder 35 rotates around the longitudinal axis C.

A plurality of (e.g., six) first rollers (inner rollers) 41 are attached to the rotatable cylinder 35. Each of the first rollers 41 is attached to the rotatable cylinder 35 via the corresponding roller shaft (corresponding one of 42). In the rotatable cylinder 35, the distal end of each roller shaft 42 is connected to the corresponding distal side shaft bearing (corresponding one of 43), and the proximal end of each roller shaft 42 is connected to the corresponding proximal side shaft bearing (corresponding one of 45). Each of the first rollers (scope rollers) 41 is rotatable (around its own central axis), with the corresponding roller shaft (corresponding one of 42) as a center. When the rotatable cylinder 35 rotates, the first rollers 41 and the roller shafts 42 rotate around the longitudinal axis C together with the rotatable cylinder 35. In the scope side connecting portion 8, each of the first rollers 41 forms a corresponding first projection (corresponding one of 40) in cooperation with the corresponding distal side shaft bearing (corresponding one of 43) and the corresponding proximal side shaft bearing (corresponding one of 45). The first projections (scope projections) 40 are away from one another around the longitudinal axis C, and each of the first projections 40 is projected toward the outer peripheral side.

The insertion section 3 is provided with a tubular covering 37 which covers the rotatable cylinder 35 and the first rollers 41 from the outer peripheral side. The covering 37 is formed of an elastic material such as rubber, and is flexible. The covering 37 forms part of the outer surface of the insertion section (scope side connecting portion 8). The distal end of the covering 37 is located on the distal side with respect to the distal end of the rotatable cylinder 35, and is fixed to the base portion 23 (coupling member 25A) by means of an adhesive member 38A. The proximal end of the covering 37 is located on the proximal side with respect to the proximal end of the rotatable cylinder 35, and is fixed to the base portion 23 (coupling member 25B) by means of an adhesive member 38B. At the distal and proximal ends of the covering 37, the base portion 23 and the covering 37 are in a liquid-tight state. With this structure, a liquid present outside the insertion section 3 is prevented from flowing into the inner peripheral side of the covering 37, and a liquid present outside the insertion section 3 is prevented from flowing into the hollow section 26 where the driving gear 27 is arranged. The rotatable cylinder 35 and the first rollers 41 can rotate (revolve) around the longitudinal axis C relative to the covering 37. The covering 37 is projected toward outer peripheral side at positions where the first projections 40 push the covering 37.

In the state where the spiral unit 10 is attached to the insertion section 3 (namely, the assistance tool side connecting portion 13 is connected to the scope side connecting portion 8), the assistance tool side connecting portion 13 (namely, the proximal portion of the spiral unit 10) covers the covering 37 from the outer peripheral side. The assistance tool side connecting portion 13 includes a tubular first connector member 46, and a tubular second connector member 47 coupled to the distal side of the first connector member 46. The first connector member 46 has an assistance-tool proximal surface 48, which serves as the proximal end of the spiral unit (assistance tool) 10. The assistance-tool proximal surface 48 faces the proximal side.

An engagement groove 56, which is depressed toward the inner peripheral side, is formed on the outer peripheral surface of the coupling member 25A of the base portion 23. The engagement groove 56 is located on the distal side with respect to the distal end of the rotatable cylinder 35. The engagement groove 56 is formed over the whole circumference around the longitudinal axis C. An engagement claw 57 projected toward the inner peripheral side is provided on the inner peripheral surface of the second connector member 47 of the assistance tool side connecting portion 13. In the state where the spiral unit 10 is attached to the insertion section 3 (namely, the assistance tool side connecting portion 13 is connected to the scope side connecting portion 8), the engagement claw 57 is in engagement with the engagement groove 56. With this structure, the spiral unit 10 is restrained from moving in the direction along the longitudinal axis C relative to the insertion section 3. Since the spiral unit 10 is restrained from moving in the direction along the longitudinal axis C relative to the insertion section 3, the spiral unit 10 does not disengage from the insertion section 3 when the spiral unit 10, to which the driving force is transmitted, is rotating around the longitudinal axis C.

A plurality of (e.g., six) second rollers (outer rollers) 51 are provided in the assistance tool side connecting portion 13. Each of the second rollers 51 is attached to the first connector member 46 and the second connector member 47 by means of the corresponding roller shaft (corresponding one of 52). In the second connector member 47, the distal end of each roller shaft 52 is connected to the corresponding distal side shaft bearing (corresponding one of 53). In the first connector member 46, the proximal end of each roller shaft 52 is connected to the corresponding proximal side shaft bearing (corresponding one of 55). Each of the second rollers (assistance tool rollers) 51 is rotatable (around its own central axis), with the corresponding roller shaft (corresponding one of 52) as a center. When the spiral unit 10 (assistance tool side connecting portion 13) rotates, the second rollers 51 and the roller shafts 52 rotate around the longitudinal axis C together with the spiral unit 10. In the assistance tool side connecting portion 13, each of the second rollers 51 forms a corresponding second projection (corresponding one of 50) in cooperation with the corresponding distal side shaft bearing (corresponding one of 53) and the corresponding proximal side shaft bearing (corresponding one of 55). The second projections (assistance tool projections) 50 are away from one another around the longitudinal axis C, and each of the second projections 50 is projected toward the inner peripheral side on the inner peripheral surface of the assistance tool side connecting portion 13.

In the state where the spiral unit 10 is attached to the insertion section 3 (namely, the assistance tool side connecting portion 13 is connected to the scope side connecting portion 8), the second projections 50 are located substantially at the same positions as the first projections 40 in the direction along the longitudinal axis C. Each of the second projections 50 is located between two of the first projections 40 in the direction around the longitudinal axis C. With this structure, when a driving force is transmitted to the rotatable cylinder 35, and the rotatable cylinder 35 and the first rollers 41 are rotated around the longitudinal axis C, each of the first projections 40 pushes the corresponding second projection (corresponding one of 50) in the rotating direction with the covering 37 located in between them. Accordingly, each of the second projections 50 of the spiral unit 10 is applied with a driving force by the corresponding first projection (corresponding one of 40) of the scope side connecting portion 8, and the spiral unit 10 rotates around the longitudinal axis C relative to the base portion 23 together with the rotatable cylinder 35 and the first rollers 41.

The spiral unit 10 rotates with the longitudinal axis C as a center in the state where the spiral fin 12 is pressed toward the inner peripheral side, so that a propulsion force toward the distal side or proximal side (in one side of the direction along the longitudinal axis C) is exerted on the insertion section 3 and the spiral unit 10. In the state where the rotatable cylinder 35 and the spiral unit 10 rotate integrally, the covering 37 is not rotated.

Coupling member 25D of the base portion 23 is provided with a supporting surface 61 which supports the spiral unit 10 attached to the insertion section 3. The supporting surface 61 forms part of the outer peripheral surface of the insertion section 3 (the scope side connecting portion 8). The supporting surface 61 is located on the proximal side with respect to the proximal end of the rotatable cylinder 35. The coupling member 25D is also provided with a flange portion 62 located on the proximal side of the supporting surface 61. The flange portion 62 is projected from the supporting surface 61 toward the outer peripheral side of the insertion section 3.

Figure 3:
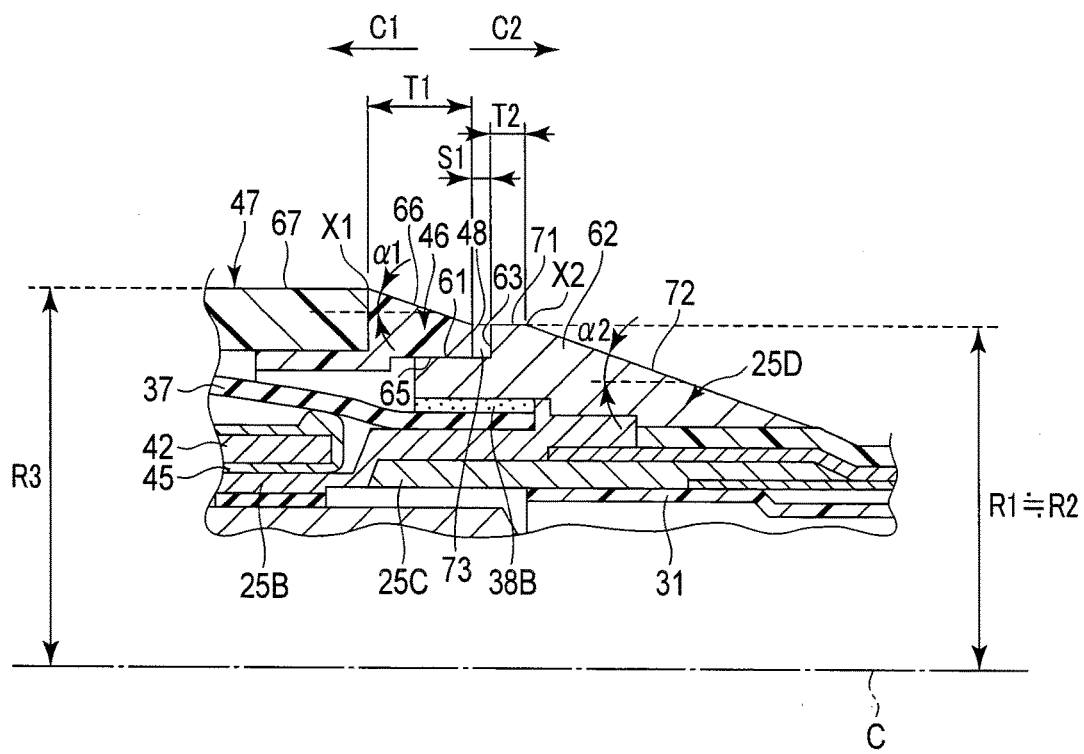
FIG. 3 is a sectional view illustrating configurations of a supporting surface, a flange portion, and their neighboring in the first embodiment, in a state where the spiral unit is attached to the insertion section.

FIG. 3 illustrates configurations of the supporting surface 61, the flange portion 72 and their neighboring in a state where the spiral unit 10 is attached to the insertion section 3 (namely, the assistance tool side connecting portion 13 is connected to the scope side connecting portion 8). As shown in FIGS. 2 and 3, the flange portion 62 is provided with an opposed surface 63 facing toward the distal side. In the present embodiment, the opposed surface 63 forms the distal surface of the flange portion 62. The opposed surface 63 forms a step between the supporting surface 61 and the flange portion 62 in a radial direction of the insertion section 3.

The inner peripheral surface of the spiral unit 10 includes a sliding surface extending from the assistance tool proximal surface 48 toward the distal side. In the state where the spiral unit 10 is attached to the insertion section 3 (namely, the assistance tool side connecting portion 13 is connected to the scope side connecting portion 8), the sliding surface 65 comes into contact with the supporting surface 61 from the outer peripheral side. When the spiral unit 10 attached to the insertion section 3 is applied with a driving force and is rotated in the above-mentioned manner, the sliding surface 65 slides on the supporting surface 61 around the longitudinal axis C.

In the state where the spiral unit 10 is attached to the insertion section 3, the opposed surface 63 of the flange portion 62 is opposed to the assistance tool proximal surface 48 of the spiral unit 10. In this state, the opposed surface 63 is located on the proximal side with respect to the assistance tool proximal surface 48. In the state where the spiral unit 10 is attached to the insertion section 3, a gap 73 is formed between the opposed surface 63 and the assistance tool proximal surface 48. In other words, the opposed surface 63 is opposed to the assistance tool proximal surface 48 with the gap 73 in the direction along the longitudinal axis C. Between the opposed surface 63 and the assistance tool proximal surface 48, the gap 73 is formed over the entire round around the longitudinal axis C. The gap 73 extends from the outer peripheral end of the assistance tool proximal surface 48 (the outer peripheral end of the opposed surface 63) toward the inner peripheral side in a radial direction of the insertion section 3. The gap 73 has a gap size S1 in the direction along the longitudinal axis C. In one example, the gap size S1 is not less than 0.1 mm and not more than 0.2 mm.

On the outer peripheral surface of the spiral unit 10 (assistance tool side connecting portion 13), an assistance tool taper surface 66 extends from the assistance tool proximal surface 48 to the distal side. The assistance tool taper surface 66 is formed such that the outer diameter of the spiral unit 10 increases from the proximal side toward the distal side. In one example, the acute angle $\alpha1$ which the assistance tool taper surface 66 forms relative to the direction along the longitudinal axis C is not less than 5° and not more than 15° in a section parallel to the longitudinal axis C.

On the outer peripheral surface of the assistance tool connecting portion 13, an assistance tool diameter-uniform surface 67 is continuous with the distal side of the assistance tool taper surface 66. In other words, the assistance tool diameter-uniform surface 67 extends from the distal end X1 of the assistance tool taper surface 66 (i.e., the boundary between the assistance tool taper surface 66 and the assistance tool diameter-uniform surface 67) toward the distal side. The assistance tool diameter-uniform surface 67 is formed such that the outer diameter of the spiral unit 10 is uniform in the direction along the longitudinal axis C. The case where the outer diameter of the spiral unit 10 is uniform throughout the whole length of the assistance tool diameter-uniform surface 67 in the direction along the longitudinal axis C includes not only the case where the outer diameter of the spiral unit 10 is constant throughout the entire length of the assistance tool diameter-uniform surface 67 in the direction along the longitudinal axis C but also the case where the outer diameter of the spiral unit 10 varies within a very small range, in which the variation is not more than a predetermined variation value, throughout the whole length of the assistance tool diameter-uniform surface 67 in the direction along the longitudinal axis C. For example, the case where the outer diameter of the spiral unit 10 varies only within a small range, in which the variation is not more than 0.5 mm, throughout the whole length of the assistance tool diameter-uniform surface 67 in the direction along the longitudinal axis C can be regarded as the case where the outer diameter of the spiral unit 10 is uniform throughout the whole length of the assistance tool diameter-uniform surface 67 in the direction along the longitudinal axis C.

It assume that the position where the proximal ends of the second projections (assistance tool projections) 50 are located in the assistance tool side connecting portion 13 is a projection proximal end position E1. In the present embodiment, the distal end X1 of the assistance tool taper surface 66 (the boundary position between the assistance tool taper surface 66 and the assistance tool diameter-uniform surface 67) is located on the proximal side with respect to the projection proximal end position E1 (second projections 50). Dimension T1 of the assistance tool taper surface 66 in the direction along the longitudinal axis C (namely, the dimension of the portion between the assistance tool proximal surface 48 and the distal end X1 of the assistance tool taper surface 66 as measured in the direction along the longitudinal axis C) is 5 mm or less.

At the opposed surface 63 of the flange portion 62 (the distal end of the flange portion 62), the flange portion 62 (insertion section 3) has outer radius R1 (outer diameter). At the assistance tool proximal surface 48 of the spiral unit 10 (the proximal end of the spiral unit 10), the spiral unit 10 has outer radius R2 (outer diameter). Outer radius R1 is nearly equal to outer radius R2. The case where the outer radius R1 of the flange portion 62 at the opposed surface 63 is nearly equal to the outer radius R2 of the spiral unit 10 at the assistance tool proximal surface 48 includes not only the case where outer radius R1 is equal to outer radius R2 but also the case where outer radius R1 and outer radius R2 are slightly different due to errors at the time of manufacture etc. For example, where the difference between outer radius R1 and outer radius R2 is 0.5 mm or less, outer radius R1 and outer radius R2 are regarded as being nearly equal. In the assistance tool diameter-uniform surface 67, the spiral unit 10 has outer radius R3 (outer diameter) and this outer radius R3 is larger than outer radius R1 and outer radius R2.

Since the outer radius R1 of the flange portion 62 at the opposed surface 63 (the distal end of the flange portion 62) is nearly equal to the outer radius R2 of the spiral unit 10 at the assistance tool proximal surface 48 (the proximal end of the assistance tool taper surface 66), no step is formed between the flange portion 62 and the assistance tool taper surface 66 in the state where the spiral unit 10 is attached to the insertion section 3. In other words, in the state where the assistance tool side connecting portion 13 is connected to the scope side connecting portion 8, the assistance tool taper surface 66 (the proximal end of the outer peripheral surface of the spiral unit 20) does not form a step relative to the flange portion 62 in the radial direction of the insertion section 3, between the assistance tool proximal surface 48 and the opposed surface 63 of the flange portion 62.

On the outer peripheral surface of the flange portion 62, a flange diameter-uniform surface 71 extends from the outer peripheral end of the opposed surface 63 (the distal end of the flange portion 62) toward the proximal side. The flange diameter-uniform surface 71 is formed such that the outer diameter of the flange portion 62 is uniform in the direction along the longitudinal axis C. The case where the outer diameter of the flange portion 62 is uniform throughout the whole length of the flange diameter-uniform surface 71 in the direction along the longitudinal axis C includes not only the case where the outer diameter of the flange portion 62 is constant throughout the entire length of the flange diameter-uniform surface 71 in the direction along the longitudinal axis C but also the case where the outer diameter of the flange portion 62 varies within a very small range, in which the variation is not more than a predetermined variation value, throughout the whole length of the flange diameter-uniform surface 71 in the direction along the longitudinal axis C. For example, the case where the outer diameter of the flange portion 62 varies only within a small range, in which the variation is not more than 0.5 mm throughout the whole length of the flange diameter-uniform surface 71 in the direction along the longitudinal axis C can be regarded as the case where the outer diameter of the flange portion 62 is uniform throughout the whole length of the flange diameter-uniform surface 71 in the direction along the longitudinal axis C.

On the outer peripheral surface of the flange portion 62, a flange taper surface 72 is continuous with the proximal side of the flange diameter-uniform surface 71. In other words, the flange taper surface 72 extends from the proximal end X2 of the flange diameter-uniform surface 71 (the boundary between the flange diameter-uniform surface 71 and the flange taper surface 72) toward the proximal side. Dimension T2 of the flange diameter-uniform surface 71 in the direction along the longitudinal axis C (namely, the dimension of the portion between the opposed surface 63 and the proximal end X2 of the flange diameter-uniform surface 66, as measured in the direction along the longitudinal axis C) is 2 mm or less. The flange taper surface 72 is formed such that the outer diameter of the flange portion 62 decreases from the distal side toward the proximal side. In one example, the acute angle α2 which the flange taper surface 72 forms relative to the direction along the longitudinal axis C is not less than 15° and not more than 25° in a section parallel to the longitudinal axis C. Therefore, the absolute value of the difference between the acute angle α1 of the assistance tool taper surface 66 and the acute angle α2 of the flange taper surface 72 is 20° or less. The outer peripheral surface of the proximal side flexible tube section 22 is continuous with the proximal end of the flange taper surface 72.

A description will now be given of the function and advantages of the endoscope device 1, namely, the insertion device of the present embodiment. When a lumen is observed using the endoscope device 1, the insertion section 3 is inserted into the spiral unit (assistance tool) 10 from its distal end, and the spiral unit 10 is moved relative to the insertion section 3 toward the proximal side along the longitudinal axis C. The spiral unit 10 is moved to the position where the assistance tool side connecting portion 13 covers the outer peripheral side of the scope side connecting portion 8, and then the assistance tool side connecting portion 13 is connected to the scope side connecting portion 8. As a result, the spiral unit (assistance tool) is attached to the insertion section 3.

After the spiral unit 10 is attached to the insertion section 3, the insertion section 3 and the spiral unit 10 are inserted into a lumen. The electric motor 16 is driven based on an operation input performed in an operation input device (not shown), and a driving force is transmitted to the spiral unit 10 in the above-mentioned manner. As a result, the spiral unit 10 is rotated around the longitudinal axis C. The spiral unit 10 rotates in the state where the spiral fin 12 is pressed toward the inner peripheral side by the wall of the lumen, so that a propulsion force toward the distal side or proximal side (in one side of the direction along the longitudinal axis C) is exerted on the insertion section 3 and the spiral unit 10. The propulsion force enhances the mobility of the insertion section 3 in the lumen. When the spiral unit 10 is detached from the insertion section 3, the assistance tool side connecting portion 13 and the scope side connecting portion 8 are disengaged from each other, and the spiral unit 10 is moved relative to the insertion section 3 toward the distal side.

In the present embodiment, in the state where the spiral unit 10 is attached to the insertion section 3, the assistance tool proximal surface 48 is opposed to the opposed surface 63 of the flange portion 62. On the inner peripheral surface of the spiral unit 10, a sliding surface 65 extends from the assistance tool proximal surface 48 toward the distal side, and when the spiral unit 10 attached to the insertion section 3 rotates, the sliding surface 65 slides on the supporting surface 61 around the longitudinal axis C. In the state where the spiral unit 10 is rotating in the lumen, filthy matter may enter the region between the sliding surface 65 and the supporting surface 61 of the scope side connecting portion 8 only through the gap 73 between the assistance tool proximal surface 48 and the opposed surface 63. For this reason, the filthy matter hardly enters the region between the sliding surface 65 and the supporting surface 61.

In the state where the assistance tool side connecting portion 13 is connected to the scope side connecting portion 8, the assistance tool taper surface 66 does not form a step relative to the flange portion 62 in the radial direction of the insertion section 3, between the assistance tool proximal surface 48 and the opposed surface 63 of the flange portion 62. Since no step is formed between the assistance tool taper surface 66 and the flange portion 62, filthy matter is hardly collected in the portion between the assistance tool proximal surface 48 and the opposed surface 63 of the flange portion 62 or in the neighborhood of that portion. For this reason, the filthy matter hardly enters the region between the sliding surface 65 and the supporting surface 61.

The filthy matter is prevented from entering the region between the sliding surface 65 and the supporting surface 61. As a result, in the state where the spiral unit 10 is rotating around the longitudinal axis C relative to the base portion 23, the sliding surface 65 properly slides on the supporting surface 61 around the longitudinal axis C. Accordingly, the spiral unit 10 properly rotates relative to the base portion 23, and reliable rotation performance of the spiral unit 10 around the longitudinal axis C can be ensured.

In the present embodiment, in the state where the spiral unit 10 is attached to the insertion section 3, a gap 73 is formed between the opposed surface 63 of the flange portion 62 and the assistance tool proximal surface 48 in the direction along the longitudinal axis C, and that gap 73 has gap dimension S1 of a certain value. With this structure, even if filthy matter enters the region between the opposed surface 63 and the assistance tool proximal surface 48, the rotation of the spiral unit 10 relative to the base portion 23 is not adversely affected.

In the present embodiment, on the outer peripheral surface of the spiral unit 10, an assistance tool taper surface 66 extends from the assistance tool proximal surface 48 to the distal side. Since the assistance tool taper surface 66 is provided, filthy matter is hardly collected in the portion between the assistance tool proximal surface 48 and the opposed surface 63 of the flange portion 62 or in the neighborhood of that portion. In addition, since the acute angle $\alpha 1$ which the assistance tool taper surface 66 forms relative to the direction along the longitudinal axis C is less than or equal to the acute angle $\alpha 2$ of the flange taper surface 72, filthy matter is hardly collected in the portion between the assistance tool proximal surface 48 and the opposed surface 63 of the flange portion 62 or in the neighborhood of that portion.

The distal end X1 of the assistance tool taper surface 66 is located on the proximal side with respect to the projection proximal end position E1 (second projections 50). With this structure, dimension T1 of the assistance tool taper surface 66 in the direction along the longitudinal axis C is small. Since dimension T1 of the assistance tool taper surface 66 in the direction along the longitudinal axis C is small, the spiral unit 10 is allowed to have a small outer diameter in the portion which is located on the distal side with respect to the assistance tool taper surface 66. Since the outer diameter of the spiral unit 10 can be made small, the insertion section 3 and the spiral unit 10 can be easily moved in the lumen.

In the present embodiment, the flange taper surface 72 of the flange portion 62 is continuous with the proximal side of the flange diameter-uniform surface 71. Since the flange taper surface 72 is provided, the outer surface of the insertion section 3 is smoothly continuous between the flange portion 62 and the proximal side flexible tube section 22, without any step in between. Since the outer surface of insertion section 3 is smoothly continuous between the flange portion 62 (scope side connecting portion 8) and the proximal side flexible tube section 22, the insertion section 3 and the spiral unit 10 can be easily moved in the lumen.

Second Embodiment

The second embodiment of the present invention will now be described with reference to FIGS. 4 and 5. The second embodiment is obtained by modifying the first embodiment, as will be described below. The same reference numerals as used in connection with the first embodiment will be used to refer to similar components, and a description of such components will be omitted.

Figure 4:
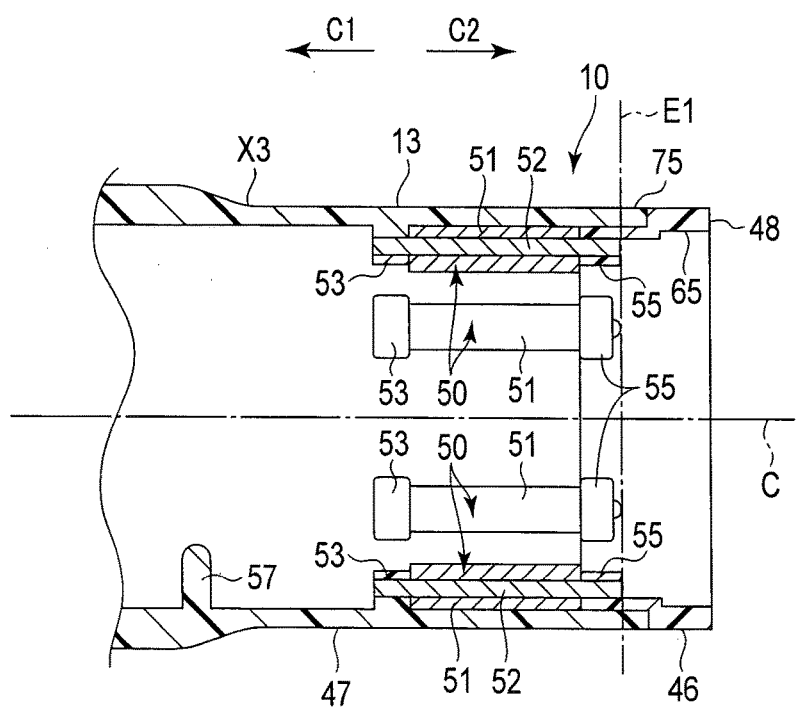
FIG. 4 is a sectional view schematically illustrating a configuration of an assistance tool side connecting portion of a spiral unit according to the second embodiment in a section parallel to the longitudinal axis.
Figure 5:
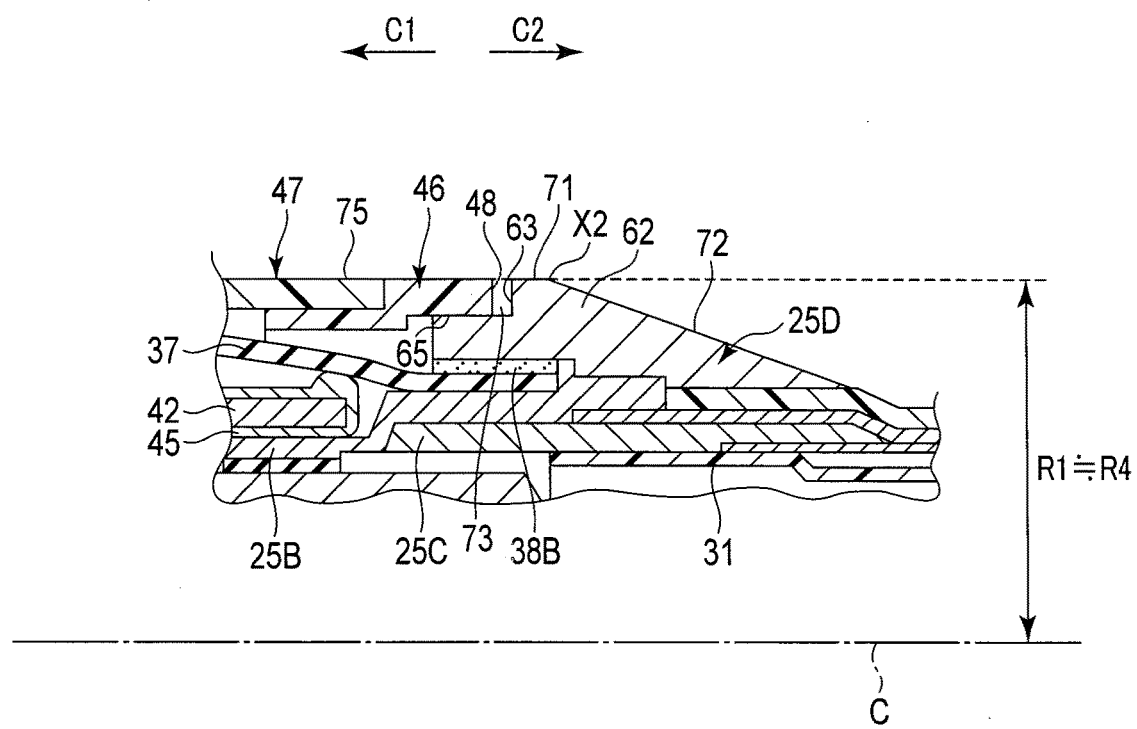
FIG. 5 is a sectional view illustrating structures of a supporting surface, a flange portion, and their neighboring in the second embodiment, in a state where the spiral unit is attached to an insertion section.

FIG. 4 shows a section parallel to the longitudinal axis C and illustrates configurations of the assistance tool side connecting portion 13 of a spiral unit 10. FIG. 5 illustrates configurations of a supporting surface 61, a flange portion 62, and their neighboring in a state where the spiral unit 10 is attached to the insertion section 3 (namely, the assistance tool side connecting portion 13 is connected to a scope side connecting portion 8). As shown in FIGS. 4 and 5, in the present embodiment, on the outer peripheral surface of the spiral unit (assistance tool) 10, an assistance tool diameter-uniform surface 75 is provided in place of the assistance tool taper surface 66, and the assistance tool diameter-uniform surface 75 extends from the assistance tool proximal surface 48 (the proximal end of the spiral unit 20) toward the distal side.

The assistance tool diameter-uniform surface 75 is formed such that the outer diameter of the spiral unit 10 is uniform in the direction along the longitudinal axis C. The case where the outer diameter of the spiral unit 10 is uniform throughout the whole length of the assistance tool diameter-uniform surface 75 in the direction along the longitudinal axis C includes not only the case where the outer diameter of the spiral unit 10 is constant over the entire length of the assistance tool diameter-uniform surface 75 in the direction along the longitudinal axis C but also the case where the outer diameter of the spiral unit 10 varies only within a very small range, in which the variation is not more than a predetermined variation value, throughout the whole length of the assistance tool diameter-uniform surface 75 in the direction along the longitudinal axis C. For example, the case where the outer diameter of the spiral unit 10 varies only within a small range, in which the variation is not more than 0.5 mm, throughout the whole length of the assistance tool diameter-uniform surface 75 in the direction along the longitudinal axis C can be regarded as the case where the outer diameter of the spiral unit 10 is uniform throughout the whole length of the assistance tool diameter-uniform surface 75 in the direction along the longitudinal axis C.

In the present embodiment, the distal end X3 of the assistance tool diameter-uniform surface 75 is located on the distal side with respect to the projection proximal end position E1 where the proximal ends of the second projections (assistance tool projections) 50 are located. The assistance tool diameter-uniform surface 75 may extend toward the distal side at least up to the proximal ends of the second projections (assistance tool projections) 50 (up to the projection proximal end position E1). In the portion located on the distal side with respect to the proximal ends of the second projections 50, the outer diameter of the spiral unit 20 on the outer peripheral surface of the spiral unit 20, may be either uniform in the direction along the longitudinal axis C or ununiform in the direction along the longitudinal axis C.

The outer radius R4 (outer diameter) on the assistance tool diameter-uniform surface 75 is nearly equal to the outer radius R1 (outer diameter) of the flange portion 62 (insertion section 3) at the opposed surface 63 of the flange portion 62 (the distal end of the flange portion 62). The case where the outer radius R1 of the flange portion 62 at the opposed surface 63 is nearly equal to the outer radius R4 of the spiral unit 10 on the assistance tool proximal surface 75 includes not only the case where outer radius R1 is equal to outer radius R4 but also the case where outer radius R1 and outer radius R4 are slightly different due to errors at the time of manufacture. For example, where the outer radius R4 of the spiral unit 20 on the assistance tool diameter-uniform surface 75 does not vary 0.5 mm or more from the outer radius R1 of the flange portion 62 at the opposed surface 63 and is therefore uniform in the direction along the longitudinal axis C, outer radius R1 and outer radius R4 are regarded as nearly equal.

Since the outer radius R1 of the flange portion 62 in the opposed surface 63 (the distal end of the flange portion 62) is nearly equal to the outer radius R4 of the spiral unit 10 in the assistance tool diameter-uniform surface 75 (the proximal end of the spiral unit 10), no step is formed between the flange portion 62 and the assistance tool diameter-uniform surface 75 in the state where the spiral unit 10 is attached to the insertion section 3. In other words, in the state where the assistance tool side connecting portion 13 is connected to the scope side connecting portion 8, the assistance tool diameter-uniform surface 75 (the proximal end of the outer peripheral surface of the spiral unit 20) does not form a step relative to the flange portion 62 in the radial direction of the insertion section 3, in a region where the assistance tool proximal surface 48 is opposed to the opposed surface 63 of the flange portion 62.

With the above structure, in the present embodiment as well, in the state where the spiral unit 10 attached to the insertion section 3 is rotating in the lumen, filthy matter may enter the region between the sliding surface 65 and the supporting surface 61 of the scope side connecting portion 8 only through the gap 73 between the assistance tool proximal surface 48 and the opposed surface 63. Since no step is formed between the assistance tool diameter-uniform surface 75 and the flange portion 62, filthy matter is hardly collected in the portion between the assistance tool proximal surface 48 and the opposed surface 63 of the flange portion 62 or in the neighborhood of that portion. Therefore, in the present embodiment as well, filthy matter is prevented from entering the region between the sliding surface 65 and the supporting surface 61. In the state where the spiral unit 10 is rotating around the longitudinal axis C relative to the base portion 23, the sliding surface 65 properly slides on the supporting surface 61 around the longitudinal axis C. Accordingly, in the present embodiment as well as the first embodiment, the spiral unit 10 properly rotates relative to the base portion 23, and reliable rotation performance of the spiral unit 10 around the longitudinal axis C can be ensured.

(Modifications)

In the embodiments described above, the flange portion 62 is provided with the flange diameter-uniform surface 71 and the flange taper surface 72, but it is not limited to this. For example, in one modification, the flange diameter-uniform surface 71 may extend in the direction along the longitudinal axis C from the distal end (the opposed surface 63) of the flange portion 62 to the proximal end thereof, and the flange taper surface 72 does not have to be provided. In another modification, the flange taper surface 72 may extend in the direction along the longitudinal axis C from the distal end (the opposed surface 63) of the flange portion 62 to the proximal end thereof, and the flange diameter-uniform surface 71 does not have to be provided. In this case as well, the flange taper surface 72 is formed such that the outer diameter of the flange portion 62 decreases from the distal side toward the proximal side. In each of these modifications, in the state where the spiral unit 10 is attached to the insertion section 3, the assistance tool proximal surface 48 forms a gap relative to the opposed surface 63 of the flange portion 62. In each of these modifications, the proximal end of the spiral unit 10 (the assistance tool taper surface 66 or the assistance tool diameter-uniform surface 75) does not form a step relative to the flange portion 62 in the radial direction of the insertion section 3, in a region between the assistance tool proximal surface 48 and the opposed surface 63 of the flange portion 62.

The number of first projections (scope projections) 40 and the number of second projections (assistance tool projections) does not have to be two or more. In one modification, only one first projection 40 may be provided, and only one second projection 50 may be provided.

In one modification, the covering (37) covering the outer peripheral sides of both the rotatable cylinder (35) and the first rollers (41) does not have to be provided. In this case, when the rotatable cylinder (35) rotates around the longitudinal axis (C), each of the first projections (40) comes into contact with the corresponding second projection (corresponding one of 50). As a result, each of the first projections (40) pushes the corresponding second projection (corresponding one of 50) in the rotating direction of the rotatable cylinder (35) and the first rollers (41), and the spiral unit (10) is rotated around the longitudinal axis (C).

In one modification, the scope side connecting portion (8) does not have to be provided with the first projections (40), and the assistance tool side connecting portion (13) does not have to be provided with the second projections (50). In this case, for example, the rotatable cylinder (35) is provided in the scope side connecting portion (8), and the outer peripheral surface of the rotatable cylinder (35) is formed as a polygonal outer peripheral surface which defines a polygonal shape in a section perpendicular to the longitudinal axis (C). In addition, the inner peripheral surface of the assistance tool side connecting portion (13) of the spiral unit (10) is formed as a polygonal inner peripheral surface which defines a polygonal shape in a section perpendicular to the longitudinal axis (C). By engaging the polygonal inner peripheral surface with the polygonal outer peripheral surface, the assistance tool side connecting portion (13) is connected to the scope side connecting portion (8), and the spiral unit (19) is attached to the insertion section (3). When the rotatable cylinder (35) rotates while the spiral unit (10) attached to the insertion section (3), a driving force is transmitted from the polygonal outer peripheral surface of the rotatable cylinder (35) to the spiral unit (10) by way of the polygonal inner peripheral surface. As a result, the spiral unit (10) is rotated around the longitudinal axis (C).

In the embodiments etc. described above, the spiral unit (10) was described as an example of an assistance tool attached to the insertion section (3), but the assistance tool is not limited to the spiral unit (20). Furthermore, in the above embodiments, the endoscope (2) was described as an example of an insertion instrument, but the insertion instrument is not limited to the endoscope (2). For example, the above-described configurations may be applied to an insertion surgery system that adopts a manipulator as an insertion instrument.

In the above embodiments etc., an insertion device (1) includes an insertion section (3) extending along the longitudinal axis (C), and an assistance tool (10) which is attached to the insertion section (3) in such a manner as to cover the outer peripheral side of the insertion section (3), and which is rotated around the longitudinal axis (C) when a driving force is transmitted thereto. The proximal end of the assistance tool (10) may be defined by the assistance tool proximal surface (48), and the outer peripheral surface of the insertion section (3) is provided with a supporting surface (61) which supports the assistance tool (10). On the inner peripheral surface of the assistance tool (10), a sliding surface (65) extends from the assistance tool proximal surface (48) toward the distal side, and when the assistance tool (10) attached to the insertion section (3) rotates, the sliding surface (65) slides on the supporting surface (61) around the longitudinal axis (C). On the proximal side of the supporting surface (61) in the insertion section (3), a flange portion (62) projected from the supporting surface (61) toward the outer peripheral side is provided. The flange portion (62) is provided with an opposed surface (63) which is opposed to the assistance tool proximal surface (48) with a gap (73) in the direction along the longitudinal axis (C) in the state where the assistance tool (10) is attached to the insertion section (3). In the state where the assistance tool (10) is attached to the insertion section (3), the proximal end of the outer peripheral surface of the assistance tool (10) does not form a step relative to the flange portion (62) in a part where the assistance tool proximal surface (48) is opposed to the opposed surface (63) of the flange portion (62).

As long as the above-mentioned configurations are met, the embodiments mentioned above may be properly modified, and they may be partially combined in a proper manner.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion device comprising:
   an insertion section extending along a longitudinal axis;
   an assistance tool attached to the insertion section to cover the insertion section from an outer peripheral side of the insertion section, the assistance tool being rotated around the longitudinal axis when a driving force is transmitted to the assistance tool;
   an assistance tool proximal surface forming a proximal end of the assistance tool;
   a supporting surface provided on an outer peripheral surface of the insertion section, the supporting surface being configured to support the assistance tool;
   a sliding surface provided on an inner peripheral surface of the assistance tool, the sliding surface extending from the assistance tool proximal surface in a distal direction, the sliding surface being configured to slide on the supporting surface, with the longitudinal axis as a center, when the assistance tool attached to the insertion section rotates around the longitudinal axis;
   a flange portion provided proximally from the supporting surface in the insertion section, the flange portion being projected from the supporting surface toward the outer peripheral side of the insertion section, the flange portion including an opposed surface opposed to the assistance tool proximal surface with a gap in a direction along the longitudinal axis in a state where the assistance tool is attached to the insertion section; and
   an assistance tool taper surface provided on an outer peripheral surface of the assistance tool, the assistance tool taper surface extending from the assistance tool proximal surface in the distal direction, an outer diameter of the assistance tool taper surface increasing from a proximal direction toward the distal direction, and in a state where the assistance tool is attached to the insertion section, the assistance tool taper surface extending from the assistance tool proximal surface while no step being formed relative to the flange portion in a part where the assistance tool proximal surface is opposed to the opposed surface,
   wherein the flange portion includes a flange taper surface, an outer diameter of the flange portion taper surface decreasing from the distal direction toward the proximal direction, and
   an acute angle of the assistance tool taper surface relative to the direction along the longitudinal axis is less than or equal to an acute angle of the flange taper surface relative to the direction along the longitudinal axis.

2. The insertion device according to claim 1, wherein the assistance tool includes an assistance tool projection located distally from the sliding surface on the inner peripheral surface, the assistance tool projection being projected toward an inner peripheral side of the assistance tool, the assistance tool projection being configured to rotate the assistance tool when the driving force is transmitted thereto from the insertion section, and
   a distal end of the assistance tool taper surface is located proximally from the assistance tool projection.

3. The insertion device according to claim 2, wherein the assistance tool includes an assistance tool diameter-uniform surface provided on the outer peripheral surface, the assistance tool diameter-uniform surface extending from the distal end of the assistance tool taper surface in the distal direction, the outer diameter of the assistance tool diameter-uniform surface being uniform in the direction along the longitudinal axis and the outer diameter of the assistance tool diameter-uniform surface being larger than an outer diameter of the flange portion in the opposed surface.

4. The insertion device according to claim 1, wherein the flange portion includes a flange diameter-uniform surface provided on the outer peripheral surface, the flange diameter-uniform surface extending from the opposed surface in the proximal direction, an outer diameter of the flange diameter-uniform surface being uniform in the direction along the longitudinal axis.

5. The insertion device according to claim 4, wherein the flange taper surface is provided on the outer peripheral surface, and a distal end of the flange taper surface is continuous with a proximal end of the flange diameter-uniform surface.

* * * * *